United States Patent [19]
Egbertson et al.

[11] Patent Number: 5,945,545
[45] Date of Patent: Aug. 31, 1999

[54] FIBRINOGEN RECEPTOR ANTAGONISTS

[75] Inventors: Melissa S. Egbertson, Ambler; George D. Hartman, Lansdale; Laura M. Vassallo, Haverton, all of Pa.

[73] Assignee: Merck & Co., Inc., Rahway, N.J.

[21] Appl. No.: 08/988,815

[22] Filed: Dec. 11, 1997

Related U.S. Application Data

[60] Provisional application No. 60/032,888, Dec. 13, 1996.

[51] Int. Cl.$^6$ .................. C07D 333/32; C07C 303/00; A61K 31/38; A61K 31/18
[52] U.S. Cl. ................ 549/65; 564/92; 564/156; 514/445; 514/604
[58] Field of Search ............... 564/92, 156; 514/604, 514/445; 549/65

[56] References Cited

U.S. PATENT DOCUMENTS

| | | |
|---|---|---|
| 5,039,805 | 8/1991 | Alig et al. |
| 5,563,158 | 10/1996 | DeGrado et al. |
| 5,648,368 | 7/1997 | Egbertson et al. ............ 564/224 |

FOREIGN PATENT DOCUMENTS

| | | |
|---|---|---|
| 0 659 743 A1 | 6/1995 | European Pat. Off. |
| 0 718 287 A2 | 6/1996 | European Pat. Off. |
| 44 46 301 A1 | 6/1996 | Germany. |
| 2 276 163 | 9/1994 | United Kingdom. |
| WO 94/22834 | 10/1994 | WIPO. |
| WO 96/16942 | 6/1996 | WIPO. |

OTHER PUBLICATIONS

Egbertson, et al., Biorganic & Medicinal Chemistry Letters, "Non–Peptide Fibrinogen Receptor Antagonists. 3. Design and Discovery . . . ", vol. 4(15), pp. 1835–1840 (1994).
Zablocki et al., Current Pharmaceutical Design, "Fibrinogen Receptor Antagonists", vol. 1, pp. 533–558 (1995).

*Primary Examiner*—Deborah C. Lambkin
*Attorney, Agent, or Firm*—Richard S. Parr; Melvin Winokur

[57] ABSTRACT

Compounds of this invention have the formula:

$$R^1N{=}C(NHR^5)\text{—}Aryl^1\text{—}Z\text{—}Aryl^2\text{—}A\text{—}B$$

and pharmaceutically acceptable salts, e.g.

17 Claims, No Drawings

FIBRINOGEN RECEPTOR ANTAGONISTS

Provisional application No. 60/032,888 Dec. 13, 1996.

BACKGROUND OF THE INVENTION

The invention relates generally to inhibition of the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A*, 84, 6471–6475, (1987), describes an Arg-Gly-Asp directed adhesion receptor expressed by human endothelial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-poly-peptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP 437 367 discloses linear polypeptide fibrinogen receptor antagonists. U.S. Pat. No. 5,256,812 discloses compounds of the $R^1$—A—$(W)_a$—X—$(CH_2)_b$—$(Y)_c$—B—Z—COOR wherein $R^1$ is a guanidino or amidino moiety and A and B are chosen from specific monosubstituted aryl or heterocyclic moieties. WO9412181 describes fibrinogen receptor antagonists such as biphenylcarboxamides.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

Compounds of this invention have the formula:

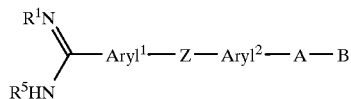

and pharmaceutically acceptable salts, e.g.

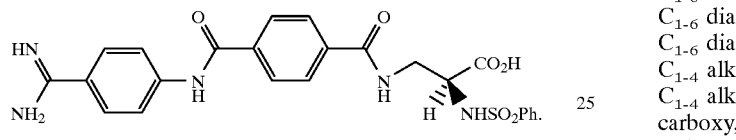

Compounds of the invention are useful for inhibiting the binding of fibrinogen to blood platelets and for inhibiting the aggregation of blood platelets. The above-mentioned compounds can be used in a method of acting upon a fibrinogen receptor which comprises administering a therapeutically effective amount of such compound to a mammal, preferably a human. A pharmaceutical composition comprising a pharmaceutically acceptable carrier and, dispersed therein, an effective amount of such compound is another feature of this invention. The use of a compound of the invention, or a pharmaceutically acceptable salt thereof, in the manufacture of a medicament for inhibiting the binding of fibrinogen to blood platelets and for inhibiting the aggregation of blood platelets in a mammal.

DETAILED DESCRIPTION OF THE INVENTION

The invention relates to a compound of the formula

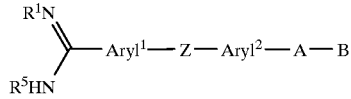

and pharmaceutically acceptable salts thereof, wherein
Aryl$^1$ and Aryl$^2$ are independently selected from
a 6-membered monocyclic aromatic ring system containing 0, 1, 2, 3, or 4 nitrogen or sulfur atoms, wherein the carbon atoms of the Aryl$^1$ ring system are either unsubstituted or substituted with R$^{2a}$, and wherein the carbon atoms of the Aryl$^2$ ring system are either unsubstituted or substituted with R$^{2b}$;
R$^{2a}$ and R$^{2b}$ are independently selected from
hydrogen C$_{1-6}$ alkyl,
carboxy,
carboxy C$_{1-6}$ alkyl-,
C$_{1-6}$ alkylcarboxy-,
C$_{1-6}$ alkylcarboxy C$_{1-6}$ alkyl-,
oxo,
C$_{1-6}$ alkyloxy-,
oxo C$_{1-6}$ alkyl-,
C$_{1-6}$ alkyloxy C$_{1-6}$ alkyl-,
hydroxy,
hydroxy C$_{1-6}$ alkyl-,
aryl,
aryl C$_{1-6}$ alkyl-, or
halogen;
R$^1$ and R$^5$ are independently selected from the group consisting of
hydrogen,
hydroxyl,
C$_{1-10}$ alkyl, C$_{3-8}$ cycloalkyl,
aryl,
aryl C$_{1-8}$ alkyl-,
amino,
amino C$_{1-8}$ alkyl-,
C$_{1-3}$ acylamino-,
C$_{1-3}$ acylamino C$_{1-8}$ alkyl-,
C$_{1-6}$ alkylamino-,
C$_{1-6}$ alkylamino C$_{1-8}$ alkyl-,
C$_{1-6}$ dialkylamino-,
C$_{1-6}$ dialkylamino C$_{1-8}$ alkyl-,
C$_{1-4}$ alkoxy-,
C$_{1-4}$ alkoxy C$_{1-6}$ alkyl-,
carboxy,
carboxy C$_{1-6}$ alkyl-,
C$_{1-3}$ alkoxycarbonyl-,
C$_{1-3}$ alkoxycarbonyl C$_{1-6}$ alkyl-,
carboxy C$_{1-6}$ alkyloxy-,
hydroxy C$_{1-6}$ alkyl-,
C$_{1-8}$ alkylcarbonyloxy C$_{1-4}$ alkyloxycarbonyl-, and
aryl C$_{1-8}$ alkylcarbonyloxy C$_{1-4}$ alkyloxycarbonyl-;
Z and A are independently chosen from
(CH$_2$)$_p$,
(CH$_2$)$_m$O(CH$_2$)n,
(CH$_2$)$_m$NR$^3$(CH$_2$)$_n$,
(CH$_2$)$_m$C(O)NR$^3$(CH$_2$)$_n$,
(CH$_2$)$_m$NR$^3$C(O)(CH$_2$)$_n$,
(CH$_2$)$_m$C(O)(CH$_2$)$_n$,
(CH$_2$)$_m$C(S)(CH$_2$)$_n$,
(CH$_2$)$_m$SO$_2$(CH$_2$)$_n$,
(CH$_2$)$_m$S(CH$_2$)$_n$,
(CH$_2$)$_m$SO(CH$_2$)$_n$,
(CH$_2$)$_m$SO$_2$NR$^3$(CH$_2$)$_n$,
(CH$_2$)$_m$C=C(CH$_2$)$_n$, and
(CH$_2$)$_m$CH(OH)(CH$_2$)$_n$,
where m and n are integers independently chosen from 0–6, p is an integer chosen from 1–6, and R$^3$ is selected from the group consisting of
hydrogen,
hydroxyl,
C$_{1-10}$ alkyl,
C$_{3-8}$ cycloalkyl,
aryl,
aryl C$_{1-8}$ alkyl-,
amino,
amino C$_{1-8}$ alkyl-,
C$_{1-3}$ acylamino-,
C$_{1-3}$ acylamino C$_{1-8}$ alkyl-,
C$_{1-6}$ alkylamino-,
C$_{1-6}$ alkylamino C$_{1-8}$ alkyl-,
C$_{1-6}$ dialkylamino-,
C$_{1-6}$ dialkylamino C$_{1-8}$ alkyl-,
C$_{1-4}$ alkoxy,
C$_{1-4}$ alkoxy C$_{1-6}$ alkyl-,
carboxy, carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and
aryl $C_{1-8}$ alkylcarbonyloxy $C_{1-4}$ alkyloxycarbonyl-;
B is

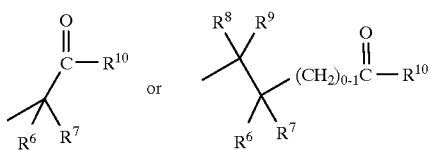

wherein $R^6$, $R^7$, $R^8$, and $R^9$ are independently chosen from:
hydrogen,
fluoro,
hydroxy $C_{1-6}$ alkyl-,
carboxy,
carboxy $C_{1-6}$ alkyl-,
hydroxyl,
$C_{1-6}$ alkyloxy-,
aryl $C_{1-6}$ alkyloxy-,
$C_{3-8}$ cycloalkyl-,
$C_{1-8}$ alkyl,
aryl,
aryl $C_{1-6}$ alkyl-,
$C_{1-6}$ alkylcarbonyloxy-,
amino,
$C_{1-6}$ alkylamino-,
amino $C_{1-6}$ alkyl-,
$C_{1-6}$ alkylamino $C_{1-6}$ alkyl-,
arylamino-,
aryl $C_{1-6}$ alkylamino-,
arylamino $C_{1-6}$ alkyl-,
aryl $C_{1-6}$ alkylamino $C_{1-6}$ alkyl-,
amino $C_{1-6}$ alkyl-,
$C_{1-6}$ dialkylamino-,
$C_{1-6}$ dialkylamino $C_{1-6}$ alkyl-,
aminocarbonyloxy-,
aminocarbonyloxy $C_{1-6}$ alkyl-,
$C_{1-6}$ alkylaminocarbonyloxy-,
$C_{1-6}$ alkylaminocarbonyloxy $C_{1-6}$ alkyl-,
aryl aminocarbonyloxy-,
aryl aminocarbonyloxy $C_{1-6}$ alkyl-,
aryl $C_{1-6}$ alkylaminocarbonyloxy-,
aryl $C_{1-6}$ alkylaminocarbonyloxy $C_{1-6}$ alkyl-,
$C_{1-8}$ alkylsulfonylamino-,
$C_{1-8}$ alkylsulfonylamino $C_{1-6}$ alkyl-,
aryl sulfonylamino-,
aryl sulfonylamino $C_{1-6}$ alkyl-,
aryl $C_{1-6}$ alkylsulfonylamino-,
aryl $C_{1-6}$ alkylsulfonylamino $C_{1-6}$ alkyl-,
$C_{1-8}$ alkyloxycarbonylamino-,
$C_{1-8}$ alkyloxycarbonylamino $C_{1-8}$ alkyl-,
aryloxycarbonylamino-,
aryloxycarbonylamino $C_{1-8}$ alkyl-,
aryl $C_{1-8}$ alkyloxycarbonylamino-,
aryl $C_{1-8}$ alkyloxycarbonylamino $C_{1-8}$ alkyl-,
$C_{1-8}$ alkylcarbonylamino-,
$C_{1-8}$ alkylcarbonylamino $C_{1-6}$ alkyl-,
arylcarbonylamino-,
arylcarbonylamino $C_{1-6}$ alkyl-,
aryl $C_{1-8}$ alkylcarbonylamino-,
aryl $C_{1-8}$ alkylcarbonylamino $C_{1-6}$ alkyl-,
aminocarbonylamino-,
aminocarbonylamnino $C_{1-6}$ alkyl-,
$C_{1-8}$ alkylaminocarbonylamino-,
$C_{1-8}$ alkylaminocarbonylamino $C_{1-6}$ alkyl-,
arylaminocarbonylamino-,
arylaminocarbonylamino $C_{1-6}$ alkyl-,
aryl $C_{1-8}$ alkylaminocarbonylamino-,
aryl $C_{1-8}$ alkylaminocarbonylamino $C_{1-6}$ alkyl-,
aminosulfonylarmino-,
aminosulfonylamino $C_{1-6}$ alkyl-,
$C_{1-8}$ alkylanminosulfonylamino-,
$C_{1-8}$ alkylaminosulfonylamino $C_{1-6}$ alkyl-,
arylaminosulfonylamino-,
arylaminosulfonylamino $C_{1-6}$ alkyl-,
aryl $C_{1-8}$ alkylaminosulfonylamino-,
aryl $C_{1-8}$ alkylaminosulfonylamino $C_{1-6}$ alkyl-,
$C_{1-6}$ alkylsulfonyl-,
$C_{1-6}$ alkylsulfonyl $C_{1-6}$ alkyl-,
aryl $C_{1-6}$ alkylsulfonyl-,
aryl $C_{1-6}$ alkylsulfonyl $C_{1-6}$ alkyl-,
$C_{1-6}$ alkylcarbonyl-,
$C_{1-6}$ alkylcarbonyl $C_{1-6}$ alkyl-,
aryl $C_{1-6}$ alkylcarbonyl-,
aryl $C_{1-6}$ alkylcarbonyl $C_{1-6}$ alkyl-,
aminocarbonyl-,
aminocarbonyl $C_{1-8}$ alkyl-,
$C_{1-8}$ alkylaminocarbonyl-,
$C_{1-8}$ alkylaminocarbonyl $C_{1-8}$ alkyl-,
arylaminocarbonyl-,
arylaminocarbonyl $C_{1-8}$ alkyl-,
aryl $C_{1-8}$ alkylaminocarbonyl-,
aryl $C_{1-8}$ alkylaminocarbonyl $C_{1-8}$ alkyl-,
aminosulfonyl-,
aminosulfonyl $C_{1-8}$ alkyl-,
$C_{1-8}$ alkylaminosulfonyl-,
$C_{1-8}$ alkylaminosulfonyl $C_{1-8}$ alkyl-,
arylaminosulfonyl-,
arylaminosulfonyl $C_{1-8}$ alkyl-,
aryl $C_{1-8}$ alkylaminosulfonyl-,
aryl $C_{1-8}$ alkylaminosulfonyl $C_{1-8}$ alkyl-,
$C_{3-8}$ cycloalkylsulfonylamino-,
thienylsulfonylamino-, and

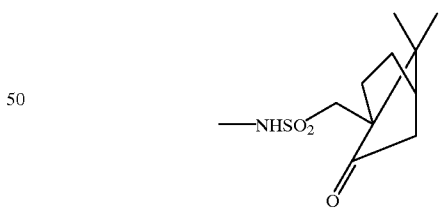

wherein groups may be unsubstituted or substituted with one or more substituents selected from $R^1$ and $R^{2a}$; and $R^{10}$ is chosen from
hydroxy,
$C_{1-8}$ alkyloxy-,
aryloxy-,
aryl $C_{1-6}$ alkyloxy-,
$C_{1-8}$ alkylcarbonyloxy $C_{1-4}$ alkyloxy-,
aryl $C_{1-8}$ alkylcarbonyloxy $C_{1-4}$ alkyloxy-.

In one class of compounds of the invention, the compounds have the formula

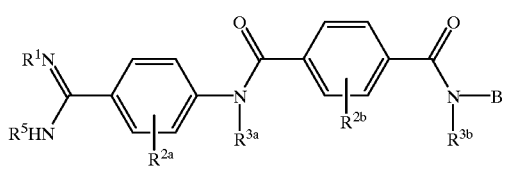

and pharmaceutically acceptable salts thereof, wherein
R$^{2a}$ and R$^{2b}$ are independently selected from the group consisting of
hydrogen
C$_{1-6}$ alkyl,
carboxy,
C$_{1-6}$ alkylcarboxy-,
carboxy C$_{1-6}$ alkyl-,
C$_{1-6}$ alkylcarboxy C$_{1-6}$ alkyl-,
oxo C$_{1-6}$ alkyl-,
C$_{1-6}$ alkyloxy-,
C$_{1-6}$ alkyloxy C$_{1-6}$ alkyl-,
hydroxy-,
hydroxy C$_{1-6}$ alkyl-,
aryl, or
aryl C$_{1-6}$ alkyl-, or
halogen;
R$^1$, R$^5$, R$^{3a}$ and R$^{3b}$ are independently selected from the group consisting of
hydrogen,
hydroxyl,
C$_{1-10}$ alkyl,
C$_{3-8}$ cycloalkyl,
aryl,
aryl C$_{1-8}$ alkyl-,
amino,
amino C$_{1-8}$ alkyl-,
C$_{1-3}$ acylamino-,
C$_{1-3}$ acylamino C$_{1-8}$ alkyl-,
C$_{1-6}$ alkylamino-,
C$_{1-6}$ alkylamino C$_{1-8}$ alkyl-,
C$_{1-6}$ dialkylamino-,
C$_{1-6}$ dialkylamino C$_{1-8}$ alkyl-,
C$_{1-4}$ alkoxy-,
C$_{1-4}$ alkoxy C$_{1-6}$ alkyl-,
carboxy,
carboxy C$_{1-6}$ alkyl-,
C$_{1-3}$ alkoxycarbonyl-,
C$_{1-3}$ alkoxycarbonyl C$_{1-6}$ alkyl-,
carboxyoxy-,
carboxy C$_{1-6}$ alkyloxy-,
hydroxy C$_{1-6}$ alkyl-,
C$_{1-8}$ alkylcarbonyloxy C$_{1-4}$ alkyloxycarbonyl-, and
aryl C$_{1-8}$ alkylcarbonyloxy C$_{1-4}$ alkyloxycarbonyl-;
B is

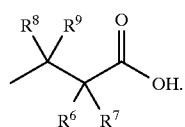

In a group of this class of compounds of the invention, the compounds have the formula

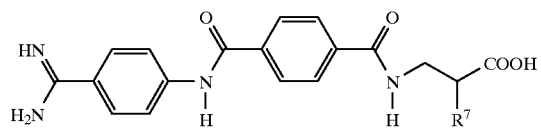

and pharmaceutically acceptable salts thereof, wherein

R$^7$ is arylsulfonylamino-, aryl C$_{1-6}$ alkylsulfonylamino-, arylsulfonylamino C$_{1-6}$ alkyl-, aryl C$_{1-6}$ alkylsulfonylamino C$_{1-6}$ alkyl-, C$_{1-8}$ alkylsulfonylamino-, C$_{1-8}$ alkylsulfonylamino C$_{1-6}$ alkyl-, C$_{3-8}$ cycloalkylsulfonylamino-, thienylsulfonylamino-, or

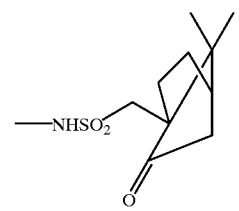

In a subgroup of this group of compounds of the invention, the compounds have the formula

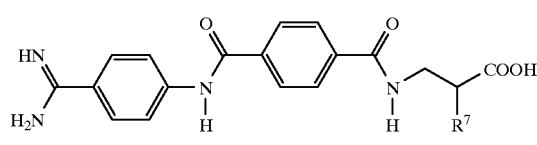

and pharmaceutically acceptable salts thereof, wherein

R$^7$ is arylsulfonylamino-, C$_{3-8}$ cycloalkylsulfonylamino-, thienylsulfonylamino-, or

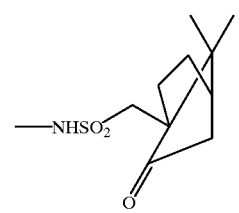

In a family of this subgroup of compounds of the invention, the compounds have the formula

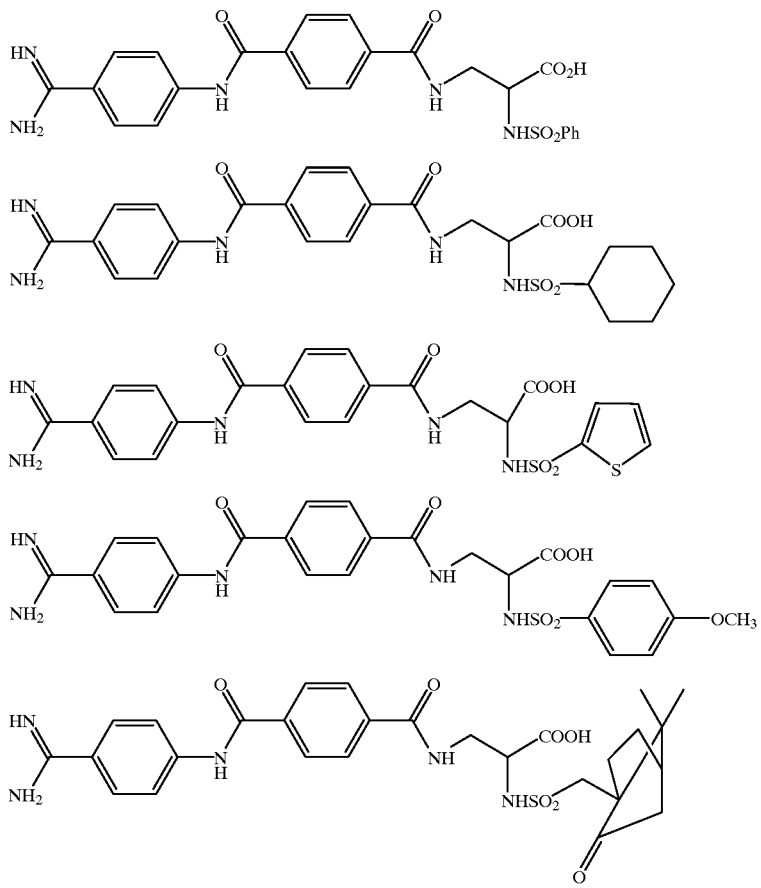

and pharmaceutically acceptable salts thereof.

A specific example of the family of compounds is compound 1-8 which is

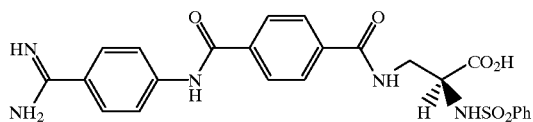

and pharmaceutically acceptable salts thereof.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Compound 1-8 was tested and found to have an $IC_{50}$ of less than 50 nM.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochioride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Compounds of the present invention are chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g., phenyl, pyridine, pyrimidine, imidazole, thiophene, oxazole, isoxazole, and thiazole.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom.

Under standard nomenclature used throughout this disclosure, the terminal portion of the designated side chain is described first followed by the adjacent functionality toward the point of attachment. For example, a methylene group substituted with benzenesulfonylamino is equivalent to

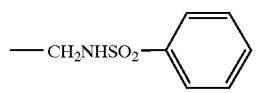

In the schemes and examples below, various reagent symbols have the following meanings:
BOC (or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
CHCl3: chloroform
BOP: Benzotriazol-1-yloxytris(dimethylamino) phosphonium, hexafluorophosphate
EDC: 1-(3-Dimethylaminopropyl)-3-ethylcarbodiimide hydrochloride
Oxone: Potassium peroxymonosulfate
LDA: Lithium diisopropylamide The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Typically, oral dosages for an adult patient are, for example, 1 mg, 10 mg or 100 mg. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be coadministered with suitable anticoagulation agents or thrombolytic agents such as plasminogen activators or streptokinase in the treatment of various vascular pathologies. They may also be combined with heparin, aspirin, or warfarin. Coadministration includes administration together or separately in order to achieve beneficial thrombosis prevention or thrombolysis.

Compounds of the invention may be prepared according to the following synthetic procedure. A derivatized 4-aminophenyliminomethyl compound having the structure

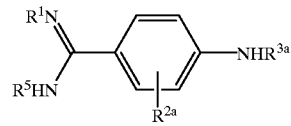

is condensed with methyl terephthalic acid to form

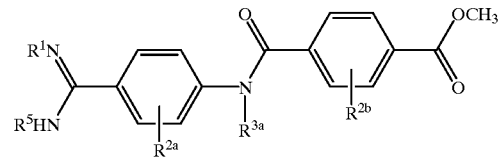

which is hydrolized to form

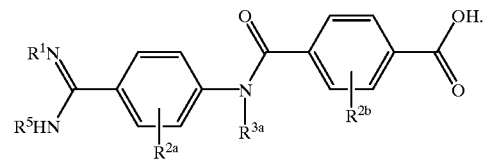

The acid is treated with $NH(R^{3b})$—B, prepared according to the procedure outlined in in WO 94/12181, scheme 19) to form

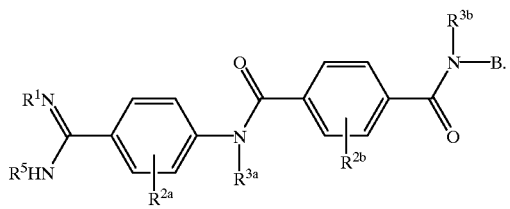

which is deprotected under acidic conditions to form the finished product.

The novel compounds of the present invention were prepared according to general procedures illustrated by the following.

EXAMPLE 1

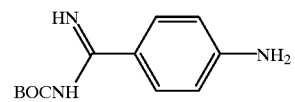

[(4-aminophenyl)iminomethyl]carbamic acid tert-butyl ester 1-2

A slurry of 4-aminobenzamidine dihydrochloride (Aldrich, 46g, 221 mmol) in THF/Dioxane (180 mL/420 mL) was treated with enough of a 1 N NaOH solution (less than 2 equivalents (442 mL)) to bring the pH of the solution to 12. A solution of di-tert-butyl dicarbonate ($BOC_2O$, Aldrich, 72.3 g, 331 mmol) in $CHCl_3$ (100 mL) was added dropwise and the pH of the reaction monitored closely with a pH meter. Additional 1 N NaOH was added as needed to maintain the pH of the solution >12 throughout the addition of the BOC$_2$O. After addition was complete TLC showed starting material remaining. An additional 0.5 equivalents (110 mmol, 24 g) of BOC$_2$O was added, again maintaining the pH of the solution >12. HPLC indicated the disappearance of starting material. The reaction was acidified to pH 3.5 with 10% KHSO$_4$, transferred to a separatory funnel and the layers separated. The organic layer was diluted with Et$_2$O and back extracted with 10% KHSO$_4$. The aqueous layers were combined and carefully basified with 50% NaOH to pH 11. A solid formed and was collected by filtration, washed with water and dried on the pump overnight to give a first crop of 1-2. The mother liquor was extracted with CHCl$_3$ until all product had been extracted and the resulting organic layers were concentrated to give a second crop of 1-2 as a white solid. Rf(5% MeOH/CHCl$_3$ saturated with NH$_3$) 0.45 $^1$H NMR (400 MHz, DMSO-d$_6$) d 9.0–8.5 (br, 1H), 7.70 (d, 2H), 6.53 (d, 2H), 5.75 (s, 2H), 1.4 (s, 9H).

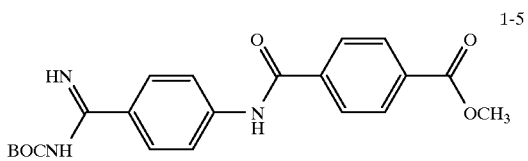

N-[4-(tert-butoxycarbonylaminoiminomethyl)phenyl]terephthalamic acid methyl ester 1-5

A slurry of methyl terephthalic acid (1-3) (Aldrich, 15 g, 83.3 mmol) in CH$_2$Cl$_2$ (400 mL) was treated with oxalyl chloride (14.5 mL, 167 mmol) and five drops of DMF and stirred at room temperature. After 1 hour the mixture became homogeneous. After a total of 1.5 hours the solution was concentrated and evaporated to give an oil that was evaporated twice more from CH$_2$Cl$_2$ to give the acid chloride 1-4 as a white solid. The acid chloride was dissolved in CHCl$_3$ (100 mL), cooled to 0° C. in a jacketed addition funnel, then added dropwise to a 0° C. slurry of 1-2 (19.6 g, 83.3 mmol), and pyridine (29 mL, 250 mmol) in CHCl$_3$ (500 mL). The resulting slurry was stirred for one hour, then treated with 1 L of 10% KHSO$_4$. The resulting precipitate was collected by filtration, then re-suspended in H$_2$O, refiltered and washed with water and dried under vacuum to give 1-5 as a white solid. Rf(5% MeOH/CHCl3 saturated with NH$_3$) 0.65. $^1$H NMR (400 MHz, DMSO-d$_6$) d 10.82 (s, 1H), 9.0 (br, 2H), 8.10 (s, 4H), 8.00 (d, 2H), 7.87 (d, 2H), 3.90 (s, 3H), 1.42 (s, 9H).

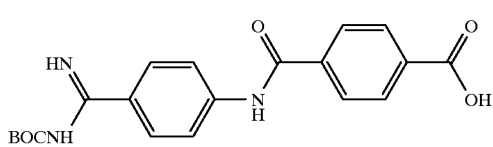

N-[4-(tert-butoxycarbonylaminoiminomethyl)phenyl]terephthalamic acid 1-6

A suspension of 1-5 (9.78 g, 2.12 mmol) in MeOH (110 mL) and THF (250 mL) was treated with 1 N NaOH solution (42.4 mL, 8.48 mmol) to give a yellow suspension that was stirred at room temperature overnight. The pH of the solution was adjusted to ~7 and the MeOH and THF carefully removed under vacuum. The resulting aqueous slurry was diluted with H$_2$O and acidified with 10% KHSO$_4$. A white solid precipitated and was collected by filtration, washed with water and Ethyl Acetate and dried under vacuum at 50° C. to give 1-6 as a white solid. $^1$H NMR (400 MHz, DMSO-d$_6$) d 11.8 (br, 1H),10.82 (s, 1H), 10.0 (br, 1H), 9.23 (s, 1H), 8.82 (s, 1H), 8.2 (s, 4H), 7.95 (d, 2H), 7.86 (d, 2H), 1.51 (s, 9H).

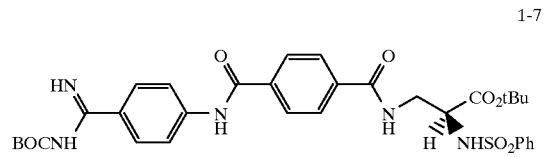

2(S)-benzenesulfonylamino-3-{4-[4-(tert-butoxycarbonylaminoimino-methyl)phenylcarbamoyl]benzoylamino}-propionic acid tert-butyl ester 1-7

A solution of 1-6 (5.0 g, 13 mmol) and 2-1 (prepared as described in WO 94/12181, scheme 19, 3.9 g, 13 mmol) in DMF (65 mL) was treated with NMM (1.44 mL, 31 mmol) and HOBT (1.8 g, 13mmol), followed by EDC (2.5 g, 13 mmol) to give a slurry. The reaction was stirred for 1 hour. The solution was diluted with EtOAc and washed with H$_2$O. 10% KHSO$_4$ was then added, resulting in a heterogeneous solution. Clear aqueous layer was collected. The remaining organic and aqueous layers were filtered and the solids washed w/10% KHSO$_4$ and ether. The solids were collected and dried overnight to yield 1-7 as a white solid. Rf(10% MeOH/EtOAc)0.21 $^1$H NMR (400 MHz, DMSO-d$_6$) d 10.56 (s, 1H), 9.0 (br, 2H), 8.67 (t, 1H), 8.2 (br, 1H), 8.03–7.87 (m, 8H), 7.7 (d, 2H), 7.5 (m, 3H), 4.05 (t, 1H), 3.5 (m, 1H), 3.4 (m,1H), 1.5 (s, 9H), 1.1(s, 9H).

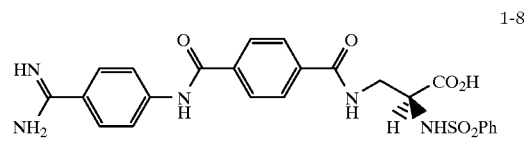

2(S)-benzenesulfonylamino-3-[4-(4-carbamimidoylphenyl-carbamoyl)benzoylamino]-propionic acid 1-8

A slurry of 1-7 (1.2 g, 1.8 mmol) in EtOAc 15 mL is cooled to −78° C. and saturated with HCL gas, warmed to 0° C. for 1 hour, then to room temperature for a total of 6 hours. The reaction was concentrated to give a tan solid that was purified by preparative HPLC to give 1-8 as the zwitterion containing 0.3 mole equivalents of TFA. Rf (10/1/1EtOH/NH$_4$OH/H$_2$O) 0.15 $^1$H NMR (400 MHz, DMSO-d$_6$) d 10.7 (s, 1H), 9.4 (bs, 2H), 9.05 (bs, 2H), 8.7 (bs, 1), 8.0 (m, 4H), 7.93 (d, 2H), 7,8 (m, 4H), 7.6–7.45 (m, 4H), 3.6 (bs, 1H), 3.5 (m, 1H), 3.4 (m, 1H).

Additional examples of compounds within the scope of the invention include those shown below:

TABLE 1

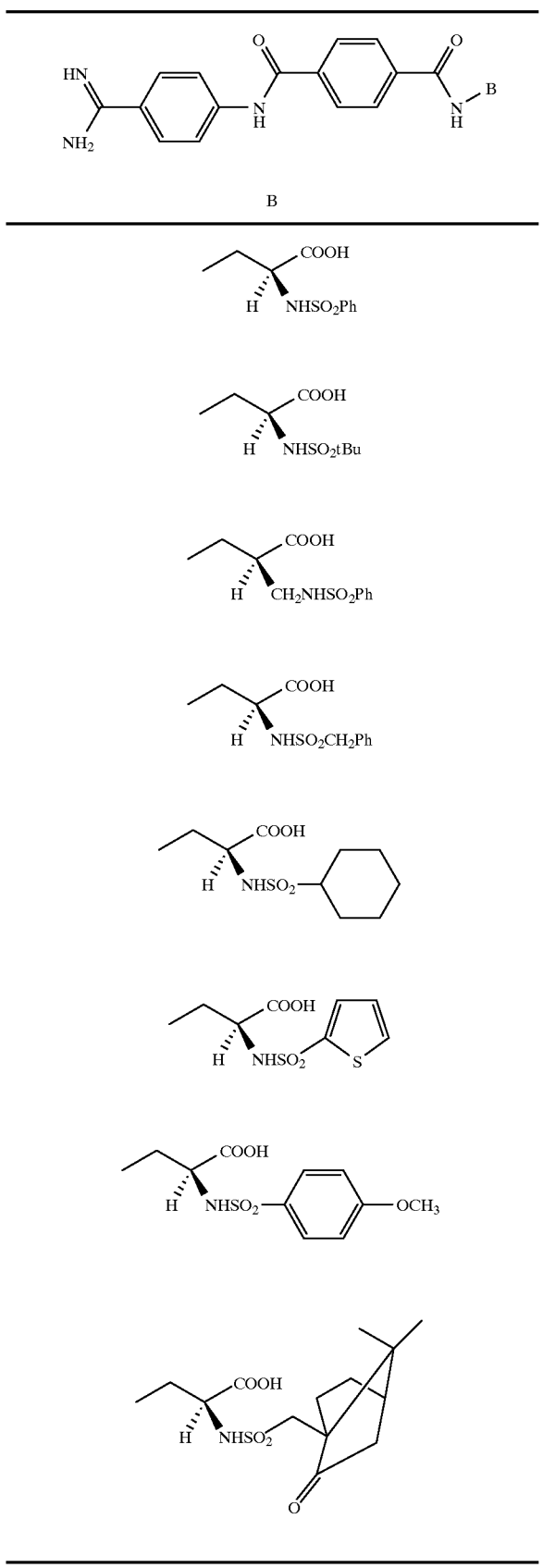

TABLE 2

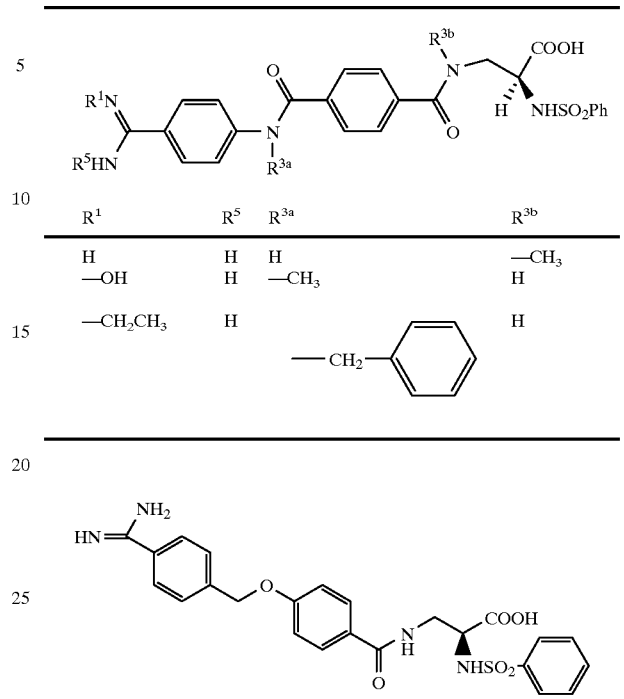

| R¹ | R⁵ | R³ᵃ | R³ᵇ |
|---|---|---|---|
| H | H | H | —CH₃ |
| —OH | H | —CH₃ | H |
| —CH₂CH₃ | H | —CH₂—C₆H₅ | H |

EXAMPLE 2

Tablet Preparation

Tablets containing 25.0, 50.0, and 100.0 mg., respectively, of the active compound 2(S)-benzenesulfonylamino-3-[4-(4-carbamimidoylphenylcarbamoyl)benzoylamino]-propionic acid are prepared as illustrated below:

| TABLE FOR DOSES CONTAINING FROM 25–100 MG OF THE ACTIVE COMPOUND | | | |
|---|---|---|---|
| | \multicolumn{3}{c}{Amount-mg} | | |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 3

Intravenous Formulations

An intravenous dosage form of the above-indicated active compound is prepared as follows:

| | |
|---|---|
| Active Compound | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 4

Intravenous Formulation

A pharmaceutical composition was prepared at room temperature using 2(S)-benzenesulfonylamino-3-[4-(4-carbamimidoylphenylcarbamoyl)benzoylamino]-propionic acid, a citrate buffer, and sodium chloride, to obtain a concentration of 0.25 mg/ml.

800 grams of water was introduced into a standard pharmaceutical mixing vessel. 0.25 grams of (3(R)-[(2-Amino-4-pyridyl)ethyl]-2-piperidon-1-yl)acetic-b-alanine was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| 2(S)-benzenesulfonylamino-3-[4-(4-carbamimidoylphenylcarbamoyl)benzoylamino]-propionic acid | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

EXAMPLE 5

In a procedure for determining potency of fibrinogen receptor antagonist following oral administration to a patient, compound 1-8 was orally administered to a dog. Blood samples were drawn at various intervals over a 6 hour period and subjected to the ADP-stimulated platelet aggregation assay.

Compound 1-8 was shown to have a profound oral profile with regard to platelet aggregation over time. According to the ADP extent measurement of percent inhibition of platelet aggregation, a dose of 0.2 mg/kg p.o. provided 100% inhibition over a period of 6 hours.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A compound of the formula

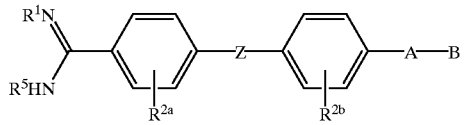

and pharmaceutically acceptable salts thereof, wherein
$R^{2a}$ and $R^{2b}$ are independently selected from
hydrogen
$C_{1-6}$ alkyl,
carboxy,
carboxy $C_{1-6}$ alkyl-,
$C_{1-6}$ alkylcarboxy -,
$C_{1-6}$ alkylcarboxy $C_{1-6}$ alkyl-,
oxo,
$C_{1-6}$ alkyloxy-,
oxo $C_{1-6}$ alkyl-,
$C_{1-6}$ alkyloxy $C_{1-6}$ alkyl-,
hydroxy,
hydroxy $C_{1-6}$ alkyl-,
aryl,
aryl $C_{1-6}$ alkyl-, or
halogen;
$R^1$ and $R^5$ are independently selected from the group consisting of
hydrogen,
hydroxyl,
$C_{1-10}$ alkyl,
$C_{3-8}$ cycloalkyl,
aryl,
aryl $C_{1-8}$ alkyl-,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino $C_{1-8}$ alkyl-,
$C_{1-6}$ dialkylamino-,
$C_{1-6}$ dialkylamino $C_{1-8}$ alkyl-,
$C_{1-4}$ alkoxy-,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and
aryl $C_{1-8}$ alkylcarbonyloxy $C_{1-4}$ alkyloxycarbonyl-;
Z and A are independently chosen from
$(CH_2)_p$,
$(CH_2)_m O(CH_2)_n$,
$(CH_2)_m NR^3 (CH_2)_n$,
$(CH_2)_m C(O)NR^3 (CH_2)_n$,
$(CH_2)_m NR^3 C(O)(CH_2)_n$,
$(CH_2)_m C(O)(CH_2)_n$,
$(CH_2)_m C(S)(CH_2)_n$,
$(CH_2)_m SO_2 (CH_2)_n$, $(CH_2)_mS(CH_2)_n$-,
$(CH_2)_mSO(CH_2)_n$-,
$(CH_2)_mSO_2NR^3(CH_2)_n$-,
$(CH_2)_mC\!\!=\!\!C(CH_2)_n$-, and
$(CH_2)_mCH(OH)(CH_2)_n$-,
where m and n are integers independently chosen from 0–6, p is an integer chosen from 1–6, and $R^3$ is selected from the group consisting of
hydrogen,
hydroxyl,
$C_{1-10}$ alkyl,
$C_{3-8}$ cycloalkyl,
aryl,
aryl $C_{1-8}$ alkyl-,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino $C_{1-8}$ alkyl-,
$C_{1-6}$ dialkylamino-,
$C_{1-6}$ dialkylamino $C_{1-8}$ alkyl-,
$C_{1-4}$ alkoxy,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and
aryl $C_{1-8}$ alkylcarbonyloxy $C_{1-4}$ alkyloxycarbonyl-;
B is

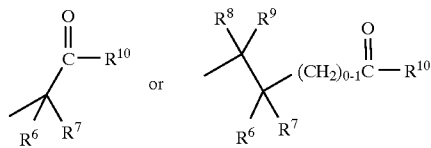

wherein $R^6$, $R^7$, $R^8$, and $R^9$ are independently chosen from:
hydrogen,
fluoro,
hydroxy $C_{1-6}$ alkyl-,
carboxy,
carboxy $C_{1-6}$ alkyl-,
hydroxyl,
$C_{1-6}$ alkyloxy-,
aryl $C_{1-6}$ alkyloxy-,
$C_{3-8}$ cycloalkyl-,
$C_{1-8}$ alkyl,
aryl,
aryl $C_{1-6}$ alkyl-,
$C_{1-6}$ alkylcarbonyloxy-,
amino,
$C_{1-6}$ alkylamino-,
amino $C_{1-6}$ alkyl-,
$C_{1-6}$ alkylamino $C_{1-6}$ alkyl-,
arylamino-,
aryl $C_{1-6}$ alkylamino-,
arylamino $C_{1-6}$ alkyl-,
aryl $C_{1-6}$ alkylamino $C_{1-6}$ alkyl-,
amino $C_{1-6}$ alkyl-,
$C_{1-6}$ dialkylamino-,
$C_{1-6}$ dialkylamino $C_{1-6}$ alkyl-,
aminocarbonyloxy-,
aminocarbonyloxy $C_{1-6}$ alkyl-,
$C_{1-6}$ alkenylaminocarbonyl-,
$C_{1-6}$ alkylaminocarbonyloxy $C_{1-6}$ alkyl-,
aryl aminocarbonyloxy-,
aryl aminocarbonyloxy $C_{1-6}$ alkyl-,
aryl $C_{1-6}$ alkylaminocarbonyloxy-,
aryl $C_{1-6}$ alkylaminocarbonyloxy $C_{1-6}$ alkyl-,
$C_{1-8}$ alkylsulfonylamino-,
$C_{1-8}$ alkylsulfonylamino $C_{1-6}$ alkyl-,
aryl sulfonylamino-,
aryl sulfonylamino $C_{1-6}$ alkyl-,
aryl $C_{1-6}$ alkylsulfonylamino-,
aryl $C_{1-6}$ alkylsulfonylamino $C_{1-6}$ alkyl-,
$C_{1-8}$ alkyloxycarbonylamino-,
$C_{1-8}$ alkyloxycarbonylamino $C_{1-8}$ alkyl-,
aryloxycarbonylamino-,
aryloxycarbonylamino $C_{1-8}$ alkyl-,
aryl $C_{1-8}$ alkyloxycarbonylamino-,
aryl $C_{1-8}$ alkyloxycarbonylamino $C_{1-8}$ alkyl-,
$C_{1-8}$ alkylcarbonylamino-,
$C_{1-8}$ alkylcarbonylamino $C_{1-6}$ alkyl-,
arylcarbonylamino-,
arylcarbonylamino $C_{1-6}$ alkyl-,
aryl $C_{1-8}$ alkylcarbonylamino-,
aryl $C_{1-8}$ alkylcarbonylamino $C_{1-6}$ alkyl-,
aminocarbonylamino-,
aminocarbonylamino $C_{1-6}$ alkyl-,
$C_{1-8}$ alkylaminocarbonylamino-,
$C_{1-8}$ alkylaminocarbonylamino $C_{1-6}$ alkyl-,
arylaminocarbonylamino-,
arylaminocarbonylamino $C_{1-6}$ alkyl-,
aryl $C_{1-8}$ alkylaminocarbonylamino-,
aryl $C_{1-8}$ alkylaminocarbonylamino $C_{1-6}$ alkyl-,
aminosulfonylamino-,
aminosulfonylamino $C_{1-6}$ alkyl-,
$C_{1-8}$ alkylaminosulfonylamino-,
$C_{1-8}$ alkylaminosulfonylamino $C_{1-6}$ alkyl-,
arylaminosulfonylamino-,
arylaminosulfonylamino $C_{1-6}$ alkyl-,
aryl $C_{1-8}$ alkylaminosulfonylamino-,
aryl $C_{1-8}$ alkylaminosulfonylamino $C_{1-6}$ alkyl-,
$C_{1-6}$ alkylsulfonyl-,
$C_{1-6}$ alkylsulfonyl $C_{1-6}$ alkyl-,
aryl $C_{1-6}$ alkylsulfonyl-,
aryl $C_{1-6}$ alkylsulfonyl $C_{1-6}$ alkyl-,
$C_{1-6}$ alkylcarbonyl-,
$C_{1-6}$ alkylcarbonyl $C_{1-6}$ alkyl-,
aryl $C_{1-6}$ alkylcarbonyl-,
aryl $C_{1-6}$ alkylcarbonyl $C_{1-6}$ alkyl-,
aminocarbonyl-,
aminocarbonyl $C_{1-8}$ alkyl-,
$C_{1-8}$ alkylaminocarbonyl-,
$C_{1-8}$ alkylaminocarbonyl $C_{1-8}$ alkyl-,
arylaminocarbonyl-,
arylaminocarbonyl $C_{1-8}$ alkyl-,
aryl $C_{1-8}$ alkylaminocarbonyl-,
aryl $C_{1-8}$ alkylaminocarbonyl $C_{1-8}$ alkyl-,
aminosulfonyl-,
aminosulfonyl $C_{1-8}$ alkyl-,
$C_{1-8}$ alkylaminosulfonyl-,
$C_{1-8}$ alkylaminosulfonyl $C_{1-8}$ alkyl-,
arylaminosulfonyl-,
arylaminosulfonyl $C_{1-8}$ alkyl-,
aryl $C_{1-8}$ alkylaminosulfonyl-,
aryl $C_{1-8}$ alkylaminosulfonyl $C_{1-8}$ alkyl-, $C_{3-8}$ cycloalkylsulfonylamino-,
thienyl sulfonylamino-, and

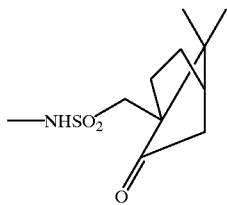

wherein groups may be unsubstituted or substituted with one or more substituents selected from $R^1$ and $R^{2a}$; and
$R^{10}$ is chosen from
hydroxy,
$C_{1-8}$ alkyloxy-,
aryloxy-,
aryl $C_{1-6}$ alkyloxy-,
$C_{1-8}$ alkylcarbonyloxy $C_{1-4}$ alkyloxy-,
aryl $C_{1-8}$ alkylcarbonyloxy $C_{1-4}$ alkyloxy-.

2. A compound of claim 1 having the formula

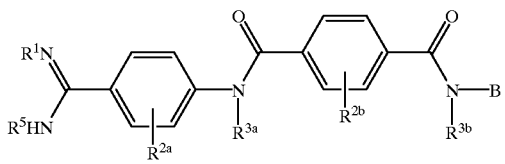

and pharmaceutically acceptable salts thereof, wherein
$R^{2a}$ and $R^{2b}$ are independently selected from the group consisting of
hydrogen
$C_{1-6}$ alkyl,
carboxy,
$C_{1-6}$ alkylcarboxy-,
carboxy $C_{1-6}$ alkyl-,
$C_{1-6}$ alkylcarboxy $C_{1-6}$ alkyl-,
oxo $C_{1-6}$ alkyl-,
$C_{1-6}$ alkyloxy-,
$C_{1-6}$ alkyloxy $C_{1-6}$ alkyl-,
hydroxy-,
hydroxy $C_{1-6}$ alkyl-,
aryl, or
aryl $C_{1-6}$ alkyl-, or
halogen;
$R^1$, $R^5$, $R^{3a}$ and $R^{3b}$ are independently selected from the group consisting of
hydrogen,
hydroxyl,
$C_{1-10}$ alkyl,
$C_{3-8}$ cycloalkyl,
aryl,
aryl $C_{1-8}$ alkyl-,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino $C_{1-8}$ alkyl-,
$C_{1-6}$ dialkylamino-,
$C_{1-6}$ dialkylamino $C_{1-8}$ alkyl-,
$C_{1-4}$ alkoxy-,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and
aryl $C_{1-8}$ alkylcarbonyloxy $C_{1-4}$ alkyloxycarbonyl-;
B is

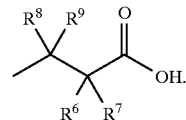

3. A compound of claim 2 having the formula

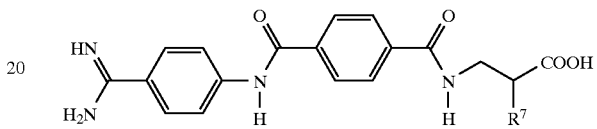

and pharmaceutically acceptable salts thereof, wherein $R^7$ is arylsulfonylamino-, aryl $C_{1-6}$ alkylsulfonylamino-, arylsulfonylamino $C_{1-6}$ alkyl-, aryl $C_{1-6}$ alkylsulfonylamino $C_{1-6}$ alkyl-, $C_{1-8}$ alkylsulfonylamino-, $C_{1-8}$ alkylsulfonylamino $C_{1-6}$ alkyl-, $C_{3-8}$ cycloalkylsulfonylamino-, thienylsulfonylamino-, or

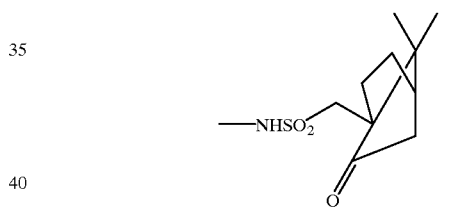

4. A compound of claim 3 having the formula

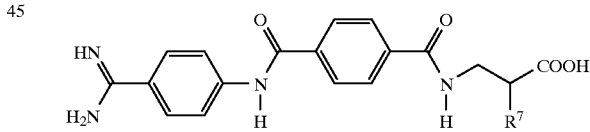

and pharmaceutically acceptable salts thereof, wherein $R^7$ is arylsulfonylamino-, $C_{3-8}$ cycloalkylsulfonylamino-, thienylsulfonylamino-, or

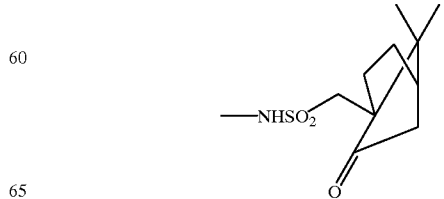

5. A compound of claim 4 having the formula

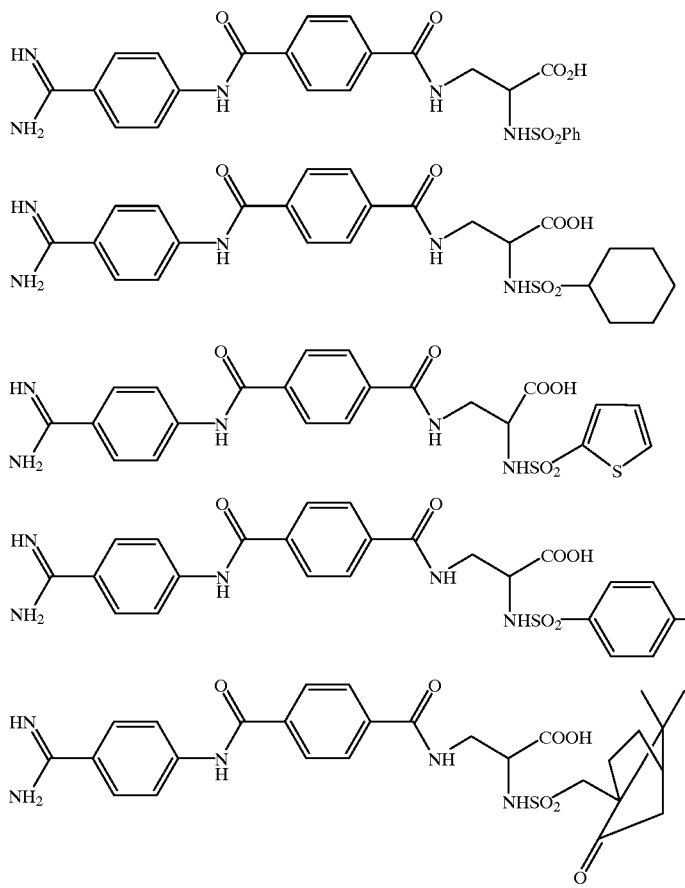

and pharmaceutically acceptable salts thereof.

6. A compound of claim 5 having the formula

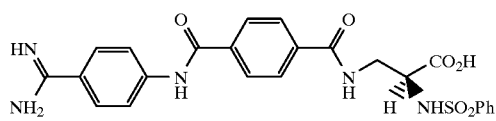

and pharmaceutically acceptable salts thereof.

7. A compound of claim 6 having the formula

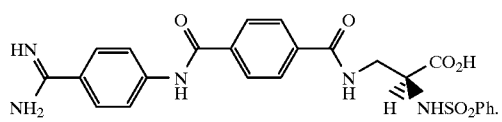

8. A compound of claim 1 for use in inhibiting the binding of fibrinogen to blood platelets, inhibiting the aggregation of blood platelets, treating thrombus formation or embolus formation, or preventing thrombus or embolus formation in a mammal.

9. A composition for inhibiting the binding of fibrinogen to blood platelets in a mammal, comprising an antifibrinogenic binding effective amount of a compound of claim 1 and a pharmaceutically acceptable carrier.

10. A method for inhibiting the binding of fibrinogen to blood platelets in a mammal, comprising treating the mammal with a composition of claim 7.

11. A method for inhibiting the aggregation of blood platelets in a mammal, by blocking fibrinogen from acting at its receptor site, comprising treating the mammal a composition of claim 9.

12. A composition for inhibiting the aggregation of blood platelets in a mammal, by blocking fibrinogen from acting at its receptor site, comprising an antifibrinogenic binding effective amount of a compound of claim 1 in combination with a thrombolytic agent and a pharmaceutically acceptable carrier.

13. A method for inhibiting the binding of fibrinogen to blood platelets in a mammal, comprising treating the mammal with a composition of claim 12.

14. A method for inhibiting the aggregation of blood platelets in a mammal, by blocking fibrinogen from acting at its receptor site, comprising treating the mammal a composition of claim 12.

15. A composition for inhibiting the aggregation of blood platelets in a mammal, by blocking fibrinogen from acting at its receptor site, comprising an antifibrinogenic binding effective amount of a compound of claim 1 in combination with an anticoagulant agent and pharmaceutically acceptable carrier.

16. A method for inhibiting the binding of fibrinogen to blood platelets in a mammal, comprising treating the mammal with a composition of claim 15.

17. A method for inhibiting the aggregation of blood platelets in a mammal, by blocking fibrinogen from acting at its receptor site, comprising treating the mammal a composition of claim 16.

* * * * *